US00PP32580P2

(12) United States Plant Patent
Schenck

(10) Patent No.: US PP32,580 P2
(45) Date of Patent: Dec. 8, 2020

(54) ***METASEQUOIA* TREE NAMED 'SOUL FIRE'**

(50) Latin Name: *Metasequoia glyptostroboides*
Varietal Denomination: Soul Fire

(71) Applicant: Andrew Schenck, Malvern, PA (US)

(72) Inventor: Andrew Schenck, Malvern, PA (US)

(73) Assignee: Plants Nouveau llc, Mobile, AL (US)

( * ) Notice: Subject to any disclaimer, the term of this patent is extended or adjusted under 35 U.S.C. 154(b) by 0 days.

(21) Appl. No.: 16/873,176

(22) Filed: Feb. 18, 2020

(51) Int. Cl.
*A01H 7/00* (2006.01)

(52) U.S. Cl.
USPC ..... Plt./213

(58) Field of Classification Search
USPC ..... Plt./213
CPC ..... A01H 7/00; A01H 5/00
See application file for complete search history.

(56) References Cited

U.S. PATENT DOCUMENTS

PP9,346 P * 10/1995 Shibata ..... Plt./213

OTHER PUBLICATIONS

Ssuu 2019-2020 Plants Nouveau New Plant Catalog, retrieved on Aug. 12, 2020, retrieved from the Internet at https://issuu.com/angelatreadwell-palmer/docs/pn_catalog_0619web_small, pp. 1, 2 and 77. (Year: 2019).*

The Geobiology and Ecology of *Metasequoia*, edited by B. LePage, C. Williams and H. Yang, vol. 22 Springer 2005, pp. 1, 4-5 and 362. (Year: 2005).*

* cited by examiner

*Primary Examiner* — June Hwu

(74) *Attorney, Agent, or Firm* — Cassandra Bright

(57) ABSTRACT

A new and distinct cultivar of *Metasequoia* tree named 'Soul Fire' is disclosed, characterized by interesting foliage colors. Spring foliage is light green and bronze, creating an overall gold appearance. Summer foliage is bright lime green and resists Summer burn. Fall foliage is orange. Internodes are shorter than typical for *Metasequoia glyptostroboides* with gold foliage. The new cultivar is a *Metasequoia*, suitable for various landscape purposes.

2 Drawing Sheets

Latin name of the genus and species: *Metasequoia glyptostroboides*.

Variety denomination: 'Soul Fire'.

BACKGROUND OF THE INVENTION

The new cultivar is a product of chance discovery by the inventor. This new variety, hereinafter referred to as 'Soul Fire', was selected as single seedling among a planting of commercial trees of unpatented, unnamed *Metasequoia glyptostroboides*. The new variety was found and selected at a commercial nursery in Malvern, Pa. during Spring of 2015.

After identifying the new variety as a potentially interesting selection, first propagation of 'Soul Fire' occurred by grafting semi-softwood tip cuttings onto standard rootstock in 2015. The inventor continued controlled testing and propagation, assessing stability of the unique characteristics of this variety. Three generations have been reproduced and have shown that the unique features of this cultivar are stable and reproduced true to type.

SUMMARY OF THE INVENTION

The cultivar 'Soul Fire' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Soul Fire' These characteristics in combination distinguish 'Soul Fire' as a new and distinct *Metasequoia* cultivar:

1. Light green and bronze Spring foliage creating a gold overall appearance.
2. Bright lime green foliage in Summer.
3. Orange Fall foliage color.
4. Shorter internodes than other gold foliage forms.
5. No Summer burn to foliage.

COMPARISON TO PARENT VARIETIES

The exact parent varieties are unknown.

COMMERCIAL COMPARISON

'Soul Fire' can be compared to the commercial variety *Metasequoia glyptostroboides* 'Golden Oji' (U.S. Plant Pat. No. 9,346) also known as 'Ogon'. The varieties are similar in most horticultural characteristics, however, trees of 'Soul Fire' differ in the following:

1. The new variety has a more compact habit with shorter growth nodes than this comparator.
2. The new variety has brighter and more consistent gold coloring than this comparator.
3. Foliage of the new variety does not burn in the Summer, while foliage of this comparator does burn in the Summer.

'Soul Fire' can be compared to the commercial variety *Metasequoia glyptostroboides* 'Amberglow', unpatented. The varieties are similar in most horticultural characteristics, however, trees of 'Soul Fire' differ in the following:

1. The new variety has a more compact habit with shorter growth nodes than this comparator.
2. The new variety has brighter and more gold coloring than this comparator.
3. Foliage of the new variety does not burn in the Summer, while foliage of this comparator does burn in the Summer.

BRIEF DESCRIPTION OF THE PHOTOGRAPHS

Figure 1:
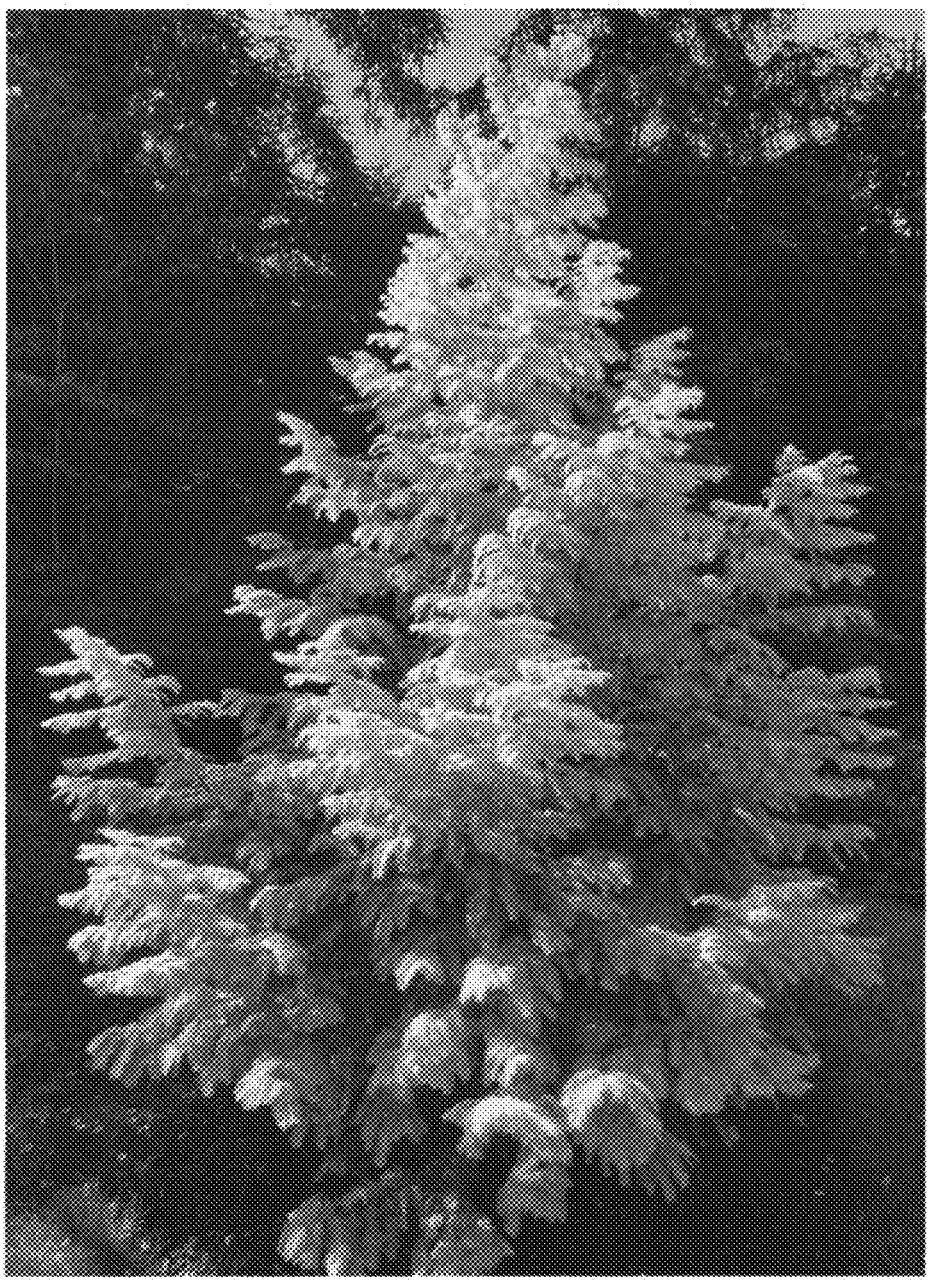

The accompanying photograph in FIG. 1 illustrates in full color a typical tree of 'Soul Fire' grown outdoors in Malvern, Pa. at approximately 4 years of age, during Summer.

Figure 2:
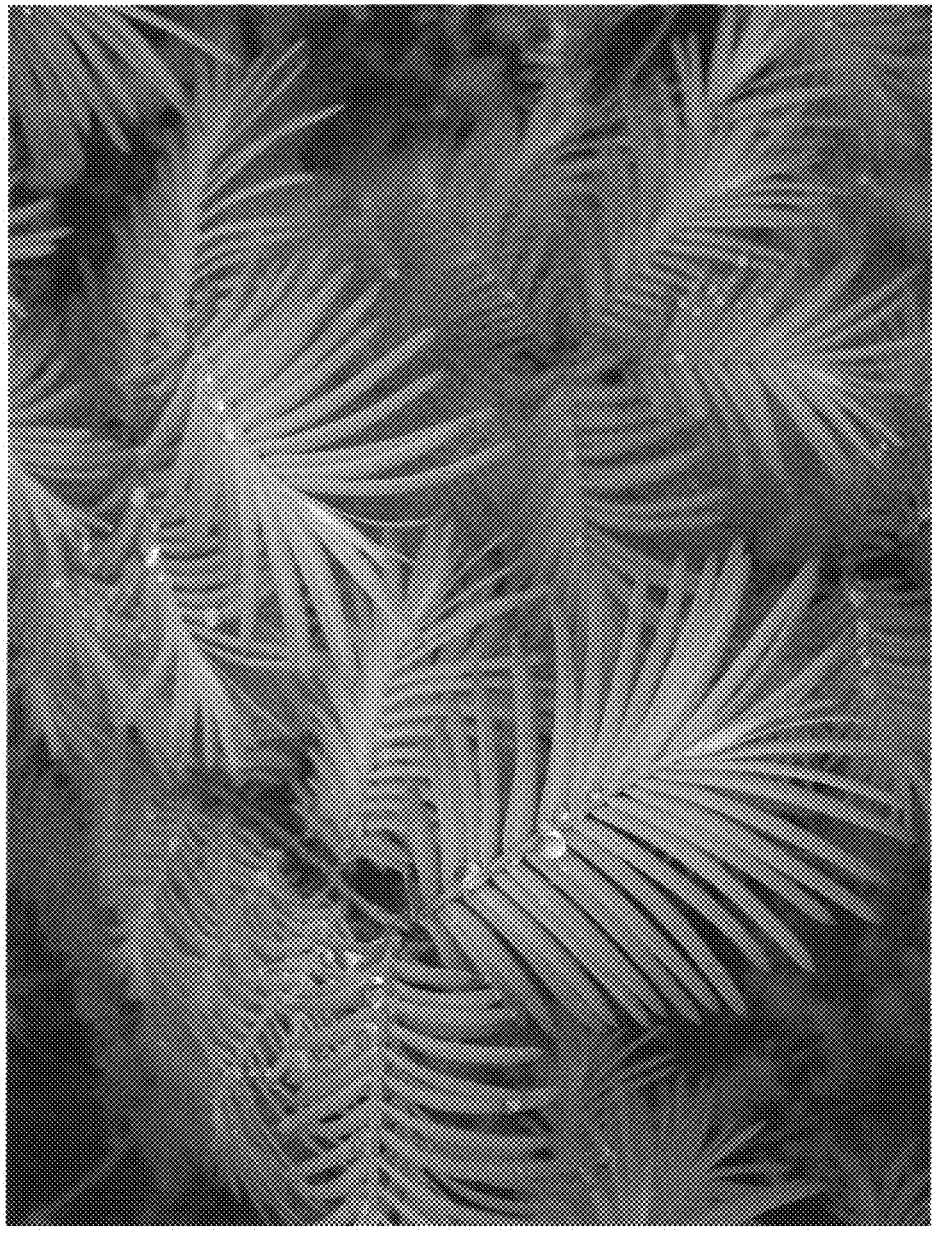

FIG. 2 illustrates a close up of the emerging Spring foliage color.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Soul Fire' trees grown outdoors in Malvern, Pa. Trees are approximately 10 years old, planted in the ground. Measurements and numerical values represent averages of typical tree types. Temperatures ranged from approximately −17° C. to 35° C. during the day and −17° C. to 26° C.

Botanical classification: *Metasequoia glyptostroboides* 'Soul Fire'.

PROPAGATION

Propagation method: Grafting.

TREE

Growth habit: Upright, pyramidal.
Deciduous or evergreen: Deciduous.
Leaf loss: Late October to December.
Leaf emergence: Mid to late April.
Height: Approximately 25 feet.
Tree spread: Approximately 12 feet.
Typical growth rate: Moderate.
Trunk color: Near RHS Greyed-Orange 175A with flaking streaks of 175B and C.
Trunk diameter (give height measured at): 12" at 8" above ground level.
Trunk texture: Exfoliating, flaking, streaked.
Branching characteristics: Horizontal from trunk.
Diameter of lateral branches: Varies, with an average range between 0.5 to 4 inches.
Quantity of lateral branches: Full branching.
Texture of lateral branches: Typical of species with shorter nodes.
Color of lateral branches: Near RHS Greyed-Orange 177B to D.
Strength of lateral branches: Strong and flexible, no snow, ice or wind damage observed.
Internode length: 2.5 cm.

FOLIAGE

Leaf:
*Arrangement*.—Opposite.
Individual needles:
*Average length*.—1.5 cm.
*Average width*.—2 mm.
*Shape of blade*.—Linear.
*Apex*.—Acute.
*Base*.—Obtuse.
*Attachment*.—Sessile.
*Margin*.—Entire.
*Texture of top surface*.—Glabrous, soft.
*Texture of bottom surface*.—Glabrous, soft.
*Color*.—Spring foliage upper side: Near RHS Yellow-Green 150C, tinted Orange-Red N34C and N34D. Very slight lint near Red 39B towards tips. Spring foliage under side: Near RHS Yellow-Green 150B, tinted Orange-Red N34C and N34D. Summer foliage upper side: Near RHS Yellow-Green N144B. Summer foliage under side: Near RHS Green 138B. Fall foliage upper side: Near RHS Yellow-Orange 19A, tips Orange 26B. Fall foliage under side: Near RHS Yellow-Orange 19A, tips Orange 26B.

FLOWER

Flowering not observed to date.
Cone not observed to date.

OTHER CHARACTERISTICS

Disease and pest resistance: Neither resistance nor susceptibility observed.
Drought tolerance: Tolerates drought once established. Can also tolerate wet conditions.
Temperature tolerance: Observed to tolerate temperatures between −17° C. and 40° C.

What is claimed is:

1. A new and distinct cultivar of *Metasequoia* tree named 'Soul Fire' as herein illustrated and described.

* * * * *